United States Patent
Zilla et al.

(10) Patent No.: US 6,540,780 B1
(45) Date of Patent: *Apr. 1, 2003

(54) POROUS SYNTHETIC VASCULAR GRAFTS WITH ORIENTED INGROWTH CHANNELS

(75) Inventors: Peter Paul Zilla, Camps Bay; Deon Bezuidenhout, Stellenbosch, both of (ZA)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,071

(22) Filed: Nov. 5, 1999

Related U.S. Application Data (60) Provisional application No. 60/109,526, filed on Nov. 23, 1998.

(51) Int. Cl.[7] .................................................. A61F 2/06
(52) U.S. Cl. ...................................... 623/1.39; 623/1.44
(58) Field of Search ................................. 623/1.1–1.22, 623/1.23, 1.25, 1.36, 1.39, 1.42, 1.44, 1.45, 1.46, 1.49; 606/108, 191, 194, 195, 198

(56) References Cited

U.S. PATENT DOCUMENTS

| | | | |
|---|---|---|---|
| 4,441,215 A | 4/1984 | Kaster ............................. 3/1.4 |
| 4,552,707 A | 11/1985 | How ............................. 264/24 |
| 4,657,544 A | 4/1987 | Pinchuk ......................... 623/1 |
| 4,743,252 A | 5/1988 | Martin, Jr. et al. .............. 623/1 |
| 4,784,659 A | 11/1988 | Fleckenstein et al. .......... 623/1 |
| 4,842,575 A | 6/1989 | Hoffman, Jr. et al. ........ 600/36 |
| 4,873,308 A | 10/1989 | Coury et al. |
| 4,902,289 A | * 2/1990 | Yanmas .......................... 623/1 |
| 4,921,495 A | 5/1990 | Kira ................................ 623/1 |
| 4,941,870 A | 7/1990 | Okada et al. ................... 427/2 |
| 5,024,671 A | 6/1991 | Tu et al. .......................... 623/1 |
| 5,037,377 A | 8/1991 | Alonso .......................... 600/36 |
| 5,108,424 A | 4/1992 | Hoffman, Jr. et al. ........... 623/1 |
| 5,132,066 A | 7/1992 | Charlesworth et al. ...... 264/184 |
| 5,197,977 A | 3/1993 | Hoffman, Jr. et al. .......... 623/1 |
| 5,415,619 A | 5/1995 | Lee et al. ....................... 600/36 |
| 5,584,875 A | 12/1996 | Duhamel et al. ............... 623/1 |
| 5,770,417 A | 6/1998 | Vacanti et al. .............. 435/180 |

OTHER PUBLICATIONS

Annis, et al., An Elastomeric Vascular Prosthesis, Trans. Am. Soc. Artif. Intern. Organs, vol. XXIV, 1978, pp209–214.

Berkowitz, Henry D, M.D. et al., Pseudointimal Development on Microporous Polyurethane Lattices, Surgery Dec. 1972, vol. 72, No. 6, pp. 888–896.

(List continued on next page.)

Primary Examiner—Michael J. Milano
Assistant Examiner—Vy Q. Bui
(74) Attorney, Agent, or Firm—Daniel Latham; Girma Wolde-Michael; Kenneth J. Collier (57) ABSTRACT

A vascular prosthesis is constructed from a structure having interconnected, helically oriented channel-porosity to allow oriented ingrowth of connective tissue into a wall of the prosthesis. The prosthesis can have a small internal diameter of 6 mm or less. Several different methods can be used to produce the prosthesis, including a fiber winding and extraction technique, a melt extrusion technique, and a particle and fiber extraction technique using either a layered method or a continuous method. Furthermore, mechanical properties of the prosthesis are matched with mechanical properties of the host vessel, thereby overcoming problems of compliance mismatch.

23 Claims, 3 Drawing Sheets-

OTHER PUBLICATIONS

Berkowitz, Henry D, M.D. et al., Pseudointimal Development on Microporous Polyurethane Lattices, *Amer. Soc. Artif. Int. Organs*, 1972 vol. XVIII pp 25–29.

Edwards, Alan et al., Development of a Microporous Compliant Small Bore Vascular Graft, *Journal of Biomaterials Applications* vol. 10—Oct. 1995, pp171–187.

Hess, F. M.D. et al., Development and Long–Term Fate of a Cellular Lining in Fibrous Polyurethane Vascular Prostheses Implanted in the Dog Carotid and Femoral Artery, *Journal of Cardiovascular Surgery*, vol. 33, 1992, pp 358–365.

Hess, F et al The Endothelialization Process of a Fibrous Polyurethane Microvascular Prosthesis After Implantation in the Abdominal Aorta of the Rat, *Journal of Cardiovascular Surgery*, vol. 24, 1983, pp. 516–524.

Hess, F et al., Seedings of Enzymatically Derived and Subcultivated Canine Endothelial Cells on Fibrous Polyurethane Vascular Prostheses, *Biomaterials*, 1992, vol. 13 No. 10, pp 657–663.

Hiratzka, Loren F. M.D. et al., In Vivo Comparison of Replamineform, Silastic, and Bioelectric Polyurethane Arterial Grafts, *Arch Surg*, vol. 114, Jun. 1979, pp 698–702.

Ives, C.L. et al. In Vivo Investigation of a New Elastomeric Vascular Graft (Mitrathane®) *Trans Am Soc Artif Intern Organs 1984*, vol. XXX, pp 587–590.

Leidner, Jacob et al., A Novel Process for the Manufacturing of Porous Grafts: Process Description and Product Evaluation, *Journal of Biomedical Materials Research*, vol. 17, 229–247.

Lyman, D.J. et al. Development of Small Diameter Vascular Prostheses, *Trans. Am. Soc. Artif. Intern. Organs,* 1977, vol. XXIII, pp 253–261.

Pollock, E. et al., Tissue Ingrowth and Porosity of Biomer, *Trans Am Soc Artif Intern Organs 1981*, vol. XXVII, pp 405–409.

Uchida, Naoki et al., Compliance Effects on Small Diameter Polyurethane Graft Patency, *Journal of Biomedical Materials Research*, vol. 27, 1269–1279 (1993).

Weber, Jon N. et al. Replamineform: A New Process for Preparing Porous Ceramic, Metal, and Polymer Prosthetic Materials, *Science*, vol. 176, May 26, 1972, pp 922–924.

White, Rodney A. et al., Preliminary Report: Evaluation of Tissue Ingrowth Into Experimental Replamineform Vascular Prostheses, *Surgery*, Feb. 1976, vol. 79, No. 2, pp 229–232.

Williams, Stuart K. et al. Formation of a Multilayer Cellular Lining on a Polyurethane Vascular Graft Following Endothelial Cell Sodding, *Journal of Biomedical Materials Research*, vol., 26, 103–117.

Wilson, G.J., Anisotropic Polyurethane Nonwoven Conduits: A New Approach to the Design of a Vascular Prostheses, *Trans Am Soc Artif Intern Organs 1983*, vol. XXIX, pp 260–268.

* cited by examiner

POROUS SYNTHETIC VASCULAR GRAFTS WITH ORIENTED INGROWTH CHANNELS

CROSS REFERENCE TO RELATED APPLICATIONS

The present application is a continuation of Provisional U.S. patent application filed Nov. 23, 1998, assigned Ser. No. 60/109,526.

FIELD OF THE INVENTION

This invention is directed to a vascular prosthesis having oriented channel-porosity to allow for oriented ingrowth of connective tissue into a wall of the prosthesis. Furthermore, mechanical properties of the prosthesis are matched with mechanical properties of a host vessel, thereby overcoming problems of compliance mismatch.

BACKGROUND OF THE INVENTION

Vascular disease in small to medium diameter arteries adversely affects arterial wall structure. As a result, blood flow through the vessel is hindered either by total occlusion or, in the opposite extreme, an acute over dilation of the vessel (aneurysm). Such indications usually require reconstructive or bypass surgery. The most successful replacements at present are autologous grafts (arteries and veins taken from the host), but often these are too diseased or unsuitable for use as an implant. There is thus a great need for the development of a reliable small diameter vascular prosthesis.

Over the last 40 years, considerable progress has been made in the development of arterial prostheses. The modern era of vascular surgery began in the early 1950's, 40 years after Carrel and Gutherie (1906) demonstrated that autologous veins could be used to replace arteries. With the advent of antibiotics and anticoagulants in ancillary medicine, the development of vascular prostheses prospered. The reversed saphenous vein was soon considered the best artery replacement and was used successfully in femoral artery replacement by Kunlin in 1949. However, the need for a smaller prosthesis led to further research by Gross and associates involving homografts using sterilized tissue. Although early results were encouraging, the long-term results were still unsatisfactory, with the grafts often failing due to thrombosis and aneurysm.

While pioneers such as Gross et al. (1948) continued to work on hetero-and homografts, Voorhees made an important observation in 1952 that changed the direction of vascular prosthetic development. After discovering that cells grew on silk thread exposed to blood, he showed the effectiveness of synthetic textile or fabric tubes as arterial replacements. A new era of vascular surgery began and the search for the most suitable material and optimal structure for a textile graft began. Experiments, even recently, have investigated factors such as knitted or woven textiles, large or small pores, different surface finishes and crimping and external reinforcing.

Presently, the materials used for vascular implants are tanned natural vessels, textile tubes made from woven or knitted Dacron, or tubes made from expanded polytetrafluoroethylene (e-PTFE). These grafts are successful for large diameter artery replacement where there is a high blood flow rate; but they have a much lower success rate in arteries with a diameter less than 6 mm. These conventional prosthetic vascular grafts do not permit unrestricted vessel ingrowth from the surrounding tissue due mostly to ingrowth spaces that are either too narrow or discontinuous. All of the present grafts eventually fail by occlusion due to thrombosis (fibrous tissue build up), or intimal hyperplasia (exuberant muscle growth at the interface between artery and graft).

Factors such as the thrombogenic nature of the graft material, surface roughness, the mechanical and haemodynamic properties of the graft and the condition of the host artery are known to influence the success of the graft. Although the reasons for failure are not fully understood, it is largely agreed that compliance mismatch between artery and graft is the predominant issue surrounding the failure of small diameter prostheses. Discontinuity in mechanical properties between the graft and artery alters the blood flow resulting in a fibrous tissue build-up leading to the complete occlusion and hence failure of the graft.

One of the main reasons for a fibrous build up on the graft is the thrombogenic reaction of the blood with the graft material. Much of the current research involves the development of various polymers, especially polyurethanes, to which biological coatings can be applied to improve the stability of the graft in the body over long periods. Ideally the graft should have an endothelial cell lining on the inner wall. This prevents a reaction by providing a less thrombogenic flow surface for the blood passing through it. One way of achieving this is through a porous graft structure. This, in conjunction with suitable biological engineering, can induce cell ingrowth through the wall leading to musculogenesis and the eventual endothelialization of the inner surface.

Autologous grafts, such as the saphenous vein and the internal mammary artery are still considered the best grafts for the reconstruction of small peripheral arteries, but these are often too diseased or unsuitable for use as a graft. None of the present textile grafts (e-PTFE and Dacron) have proved successful for long periods. Many approaches to graft production have been developed in an effort to create a porous polyurethane artery graft. Indeed, it has been shown that it is possible to create an initially compliant porous graft. However, the long-term success of such grafts remains to be proven. It has become apparent that the current methods of graft construction are ineffectual and a new approach is necessary.

It is evident that the present small diameter grafts do not provide an acceptable long-term patency. Although the causes for failure are not immediately clear, it is apparent that none of the previous prostheses have the same structure as an artery or behave mechanically as an artery does. Apart from the biological issues, which are arguably the most important and complex issues in graft design, one of the central issues involves understanding the mechanics of arterial behavior. Recent investigations have addressed the issue of compliance in an effort to create a structurally similar graft, but compliance alone has not proved completely successful. Thus, there is a need to develop a graft that addresses the issue of mechanical behavior through structure. The graft structure should create an optimal strain environment that will facilitate and encourage the development and maintenance of endothelial and smooth muscle cells in the vessel.

SUMMARY OF THE INVENTION

The present invention is directed to a synthetic vascular graft with helically oriented, interconnected transmural ingrowth channels. Vascular tissues are mostly helically arranged in the walls of natural arteries. This invention allows for helically oriented ingrowth of connective tissue into walls of synthetic graft prostheses in order to simulate mechanical properties of natural vessels.

Several different methods can be used to produce the graft of the present invention. In one method, a tube is fashioned from a graft material by coating an extractable fiber with a solution containing a biocompatible material including the graft material, and then winding the fiber onto a mandrel in a winding device. Precipitation of the solution and extraction of the fiber renders a tubular structure containing helically oriented, interconnected transmural ingrowth channels in the tube wall suitable for use as a synthetic, small-diameter vascular graft prosthesis.

In another method, a paste comprising a polymer solution and an extractable filler is prepared and deposited in a layer onto a mandrel. An extractable fiber is also wound onto the mandrel. The paste and fiber can be applied to the mandrel either simultaneously or successively alternating between the paste and the fiber, until a desired thickness of the graft is achieved. Precipitation of the solution and extraction of the fiber produces the graft of the invention.

An alternative method for making the invention involves melt extrusion of a polymer containing strands of soluble fiber, with or without physically or chemically blowing a foamed tube.

With the foregoing in mind, it is a feature and advantage of the invention to provide a synthetic vascular graft wherein mechanical properties of the graft are matched with mechanical properties of the host vessel, thereby overcoming problems of compliance mismatch.

It is another feature and advantage of the invention to provide a synthetic vascular graft that contains helically oriented, interconnecting, transmural ingrowth channels.

It is a further feature and advantage of the invention to provide a method for producing a synthetic vascular graft that contains helically oriented, interconnecting, transmural ingrowth channels.

DEFINITIONS

The term "extractable fiber" means any polymeric or other fiber material that is soluble and extractable by a solvent other than the solvent used for the graft material. The fiber has a diameter ranging in size from 10 to 300 micrometers, more preferably from 40 to 110 micrometers. The standard deviation of fibers used in this invention is typically less than 20 micrometers, more preferably less than 10 micrometers. Examples of suitable materials include alginate, gelatin, carbohydrates (sugar, dextrose, etc.), inorganic and organic salts. Water soluble fibers are suitable when water is the precipitation solvent and the fiber extractor.

The term "fiber extraction solvent" means any solvent capable of dissolving the extractable fiber without adversely affecting the graft structure. For example, water is a suitable fiber extraction solvent for water soluble fibers.

The term "non-extractable fiber" means any polymeric or other fiber material that is not extractable by the fiber extraction solvent. The fiber is either elastic or non-elastic non-degradable material, or a combination of elastic and non-elastic materials. Additionally, a reinforcing material that is either elastic or non-elastic, and is degradable in vivo, can be used in combination with the non-degradable material to provide initial strength to the graft. The non-extractable fiber typically has a diameter ranging in size from 10 to 100 micrometers. Examples of suitable non-elastic, non-degradable materials include polyethylene terephthalate (PET, Dacron) and polytetrafluoroethylene (PTFE). Examples of suitable elastic non-degradable materials include thermoplastic polyurethanes, e.g. M48, Pellethane (or clones), Biomer (or clones), or any other biocompatible elastomer. Degradable polyurethanes can serve as degradable reinforcing fibers.

The term "precipitation solvent" means any solvent that is capable of precipitating the graft material from solution. The precipitation solvent and the graft material solvent are usually miscible in all proportions. Examples of suitable precipitation solvents include: water, ethanol, acetone, or combinations of any of these. The fiber extraction solvent and the precipitation solvent may or may not be the same solvent.

The term "graft material" means any polymeric or other material that can be dissolved in a suitable solvent and re-solidified after graft manufacture by air-drying, phase inversion, or combinations thereof. Examples of suitable graft materials include: thermoplastic elastomers including thermoplastic polyurethanes, e.g. Pellethane, Biomer type polyurethanes, Chronoflex, and Hydrothane. In particular, a polyurethane developed by Medtronic and described in U.S. Pat. No. 4,873,308 is an example of a suitable graft material.

The term "graft material solvent" means any solvent capable of dissolving the graft material. Examples of suitable solvents for polyurethanes include: N-methyl pyrrolidone (NMP), N,N dimethyl diacetamide (DMAC), 1,4 dioxane, etc.

The term "graft material solution" means a solution of the graft material in the graft material solvent in concentrations ranging from 1 to 40% by mass, more typically 5 to 30% by mass, usually 10 to 25% by mass.

The term "graft material paste" means an admixture consisting of a graft material solution and an extractable filler. The ratio of filler to polymer in the solution can range from 20:1 to 1:1, more typically from 10:1 to 5:1 (ratios by mass).

The term "chemical blowing agent" means any material that decomposes to form a gas, e.g. $CO_2$ or $N_2$, wherein the gas creates pores in the graft material. Examples of chemical blowing agents include sodium bicarbonate and azodicarbonamides.

The term "physical blowing agent" means either a liquid or a gas that is introduced to molten graft material under pressure, wherein evaporation of the liquid or expansion of the gas creates bubbles that form pores in the graft material. Examples of physical blowing agents include: chloro-fluoro carbons (e.g. freon), pentane, and hexane.

The term "extractable filler" means any polymeric or other filler material that is soluble and/or extractable by a solvent other than the solvent used for the graft material. The material is preferably spherical in shape with average diameters ranging in size from 10 to 300 micrometers, more preferably from 40 to 110 micrometers. The standard deviation of the diameters of the pores is typically less than 20 micrometers, more preferably less than 10 micrometers. Examples of suitable materials include protein beads, e.g. alginate, gelatin, carbohydrates (sugar, dextrose, etc.), inorganic and organic salts. Water soluble fillers are suitable when water is the precipitation solvent and the filler extractor.

DETAILED DESCRIPTION OF THE PRESENTLY PREFERRED EMBODIMENTS

This invention is directed to an improved prosthetic vascular graft having a synthetic scaffold of transmural ingrowth channels which are characterized by an interconnected, helical orientation. A process of producing such channels in a synthetic scaffold can be achieved using an extractable fiber. The product and process are explained in detail below.

In order to promote ingrowth of connective tissue, it is important that mechanical properties of the graft are closely matched with mechanical properties of a host vessel, thereby overcoming problems of compliance mismatch. Although structure of blood vessels varies through a body, a "typical" artery consists of three distinct layers, each performing specific basic functions. An intima, consisting of an endothelium attached to a basement membrane, provides a non-thrombogenic blood contacting surface. A media contains smooth muscle cells (SMC's) as well as elastic and other intercellular connective and matrix materials, and supplies two other important properties to a blood vessel, namely compliance and contractility. In order to achieve these properties, tissues are oriented in a helical fashion in this medial layer. Another important property, namely structural integrity, is provided by an adventitia. A configuration of collagen fibers in the adventitia provides for "stiffening" of the vessel when subjected to high internal pressures, i.e. a decrease in compliance with increased strain.

The graft of the present invention has helically oriented, interconnected, transmural ingrowth channels that correspond to the helical arrangement of vascular tissues in the walls of natural arteries. The graft structure thereby creates an optimal strain environment that facilitates and encourages the development and maintenance of endothelial and smooth muscle cells in the vessel. By getting the smooth muscle cells to grow helically on the graft along the spiral channels, the graft acquires radial compliance and behaves like a real blood vessel. To achieve high porosity, the channels should be arranged at a very narrow angle, for example a 200 micron pitch. For larger wind angles, for example a 10 mm pitch, multiple fibers, all the same or a combination of soluble and reinforcing, can be wound around the graft to form corresponding channels. The pitch can be varied through the thickness of the wall by increasing or decreasing the pitch at a predefined rate as one builds up the graft wall, or alternating between two or more pitches in alternate layers. Preferably, the channels have diameters in a range of 10–300 μm, more preferably in a range of 40–110 μm.

In designing the vascular prosthesis of the invention to result in formation of a neo-artery mimicking the properties of a natural vessel, material for the scaffold should have biostability, processability, availability, and desirable mechanical properties. The porous scaffold should provide high porosity for maximal cell ingrowth and minimal bulk compressibility (to allow for compressibility associated with contractility). The prosthesis should have structural integrity and viscoelastic properties similar to those observed for natural vessels. Furthermore, in order to minimize foreign body reaction and to encourage differential cell ingrowth, the scaffold materials should also exhibit long-term in-vivo stability. Examples of suitable scaffold materials include thermoplastic elastomers, particularly thermoplastic polyurethanes.

Because of their unique combination of physical, chemical and biocompatible properties, polyurethanes are preferred for use as the primary scaffold material in the vascular graft of the invention. Enzymatic hydrolysis, auto-oxidation, mineralization, and biologically induced environmental stress cracking of polyester- and polyetherurethanes have led manufacturers of medical polyurethanes to develop more specialized formulations to prevent these occurrences. Examples of particularly suitable medical polyurethanes include Pellethane, Biomer type polyurethanes, Chronoflex, and Hydrothane.

Helical channels are formed in the vascular graft by winding an extractable fiber into the graft material before the graft is set. Fibers suitable for forming the channels include alginate, gelatin, carbohydrates, inorganic and organic salts. Selection of a suitable fiber material to create the channels requires careful consideration. The fibers can be round, flattened round, or elliptical. A flattened round fiber provides superior interconnectivity, but can be difficult to wind.

A multifactorial method (phase inversion/precipitation) can be used to solidify the scaffold material around the fibers. The solution properties of the fiber material are vital parameters in the process because the fiber material must be able to be solidified within the scaffold material and then extracted with a solvent while the scaffold material remains intact. The extractable fiber material should be non-soluble in the solvent used to dissolve the scaffold material, readily soluble in the precipitation solution, processable into fibers, and non-toxic. Furthermore, the fiber material should have sufficient melt strength to be drawn down to desired dimensions (within about ±10 μm of the desired dimensions) and be strong enough in the fiber form to withstand winding. An additional, non-extractable fiber can be used in the graft of the invention to provide structural reinforcement.

The vascular graft of the present invention can be achieved by forming interconnecting, helically oriented channels in a wall of an elastomeric polymeric tubular structure using extractable fibers to form the channels. Suitable extractable fibers include those made from alginate, gelatin, carbohydrates, inorganic and organic salts. The fibers should have diameters of 10 to 300 micrometers, more preferably 40 to 110 micrometers. Several different methods can be used to produce these grafts.

Figure 1:
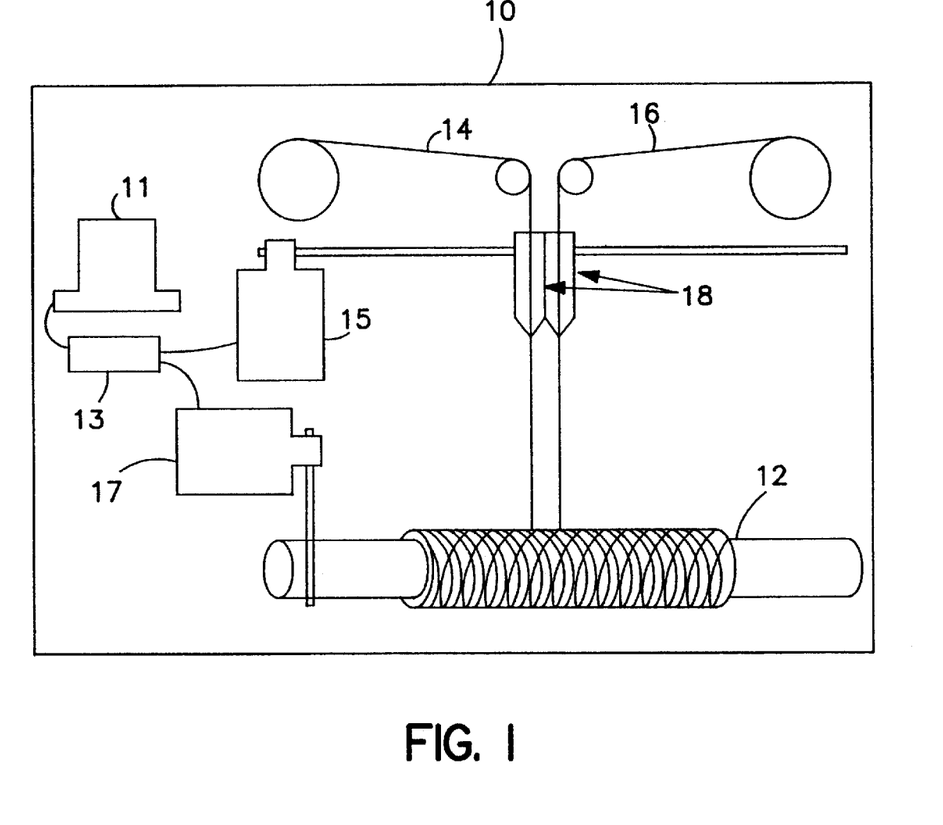
FIG. 1 is a schematic drawing of a preferred method of producing the synthetic vascular graft of the invention.

The most preferred method for producing the graft of the present invention is a fiber winding and extraction technique. This method is illustrated in FIG. 1. The method involves assembling a mandrel 12 in a custom-designed winding device 10. The device 10 can be as simple as a personal computer 11 attached to a controller 13 which is further attached to two motors 15 and 17. One motor 15 drives translational movement of the fiber 14, while the other motor 17 drives rotation of the mandrel 12. The device 10 allows for accurate control over winding speed and position of the rotating mandrel 12 and translational movement of the fiber 14, thereby allowing for the accurate placement of wound fibers on the mandrel 12. The mandrel 12 has a diameter corresponding to a desired internal diameter of a resulting graft. The internal diameter of the graft is preferably between 1 mm and 20 mm, more preferably in the range of 2 to 6 mm for small diameter vessel replacement.

Once the winding device 10 is assembled, an extractable fiber 14 is coated with a solution 18 containing a biocompatible material. The extractable fiber 14 is made of alginate, gelatin, carbohydrates, or other soluble polymers, for example. The coating solution 18 includes a suitable graft material dissolved in a suitable graft material solvent. The coating solution may additionally contain soluble particulate fillers, such as microbeads, allowing for the creation of both spherical and channel-like porosity in the same graft. Suitable graft materials include thermoplastic elastomers, particularly thermoplastic polyurethanes, such as Pellethane, Biomer type polyurethanes, Chronoflex, Hydrothane, Estane, Elast-Eon, Texin, Surethane, Corethane, Carbothane, Techoflex, Tecothane and Biospan. Suitable graft material solvents for polyurethanes include N-methyl pyrrolidone (NMP), N,N dimethyl diacetamide (DMAC), 1,4 dioxane, etc. Concentration of the graft material in the graft material solvent ranges from 1 to 40% by mass, more typically 5 to 30% by mass, usually 10 to 25% by mass. The concentration depends on various factors, including composition of the graft material, composition of the graft material solvent, and viscosity of the solution. After the fiber 14 is coated, the fiber 14 is wound onto the mandrel 12.

An additional non-extractable fiber 16 can also be wound onto the mandrel 12 for reinforcement. The non-extractable fiber 16 can be either elastic or non-elastic, or a combination of elastic and non-elastic materials. Additionally, a reinforcing material that is either elastic or non-elastic, and is degradable in vivo, can be used in combination with the non-degradable material to provide initial strength to the graft. The reinforcement material that is degradable in vivo degrades as the graft is populated by ingrowing cells and accompanying extracellular matrix material. Ingrowing material tends to stiffen the graft; therefore, a degradable fiber can be used to give initial strength to the graft without making the graft overly stiff after ingrowth. The non-extractable fiber 16 typically has a diameter ranging in size from 10 to 100 micrometers. Examples of suitable non-elastic non-degradable materials include polyethylene terephthalate (PET, Dacron) and polytetrafluoroethylene (PTFE). Examples of suitable elastic, non-degradable materials include thermoplastic polyurethanes, e.g. M48, Pellethane (or clones), Biomer (or clones), or any other biocompatible elastomer. Degradable polyurethanes can serve as degradable reinforcing fibers 16.

Tension on the extractable fibers 14 ensures "touching" of intersecting fiber strands, thereby ensuring communication between helical channels when the fibers 14 are extracted. The coating solution 18 is then solidified by phase precipitation, wherein the graft is immersed into a precipitation solvent, and/or by drying. Examples of suitable precipitation solvents include water, ethanol, acetone, or combinations of any of these. The extractable fiber 14 is extracted by applying a fiber extraction solvent to produce channels in the space occupied by the fiber 14.

Another method for producing the graft of the invention is a melt extrusion technique with oriented fibers. In this method, a molten graft material containing chopped strands of extractable fibers is extruded from an extrusion die specially adapted to orient fibrous fillers in an extrudate. The extrusion results in a tubular structure having an internal diameter preferably between 1 mm and 20 mm, more preferably in a range of 2 to 6 mm for small diameter vessel replacement. The graft material can also contain additional, non-extractable fibers for reinforcement. Physical and/or chemical blowing agents can be used to produce a foamed graft. In addition to choosing a suitable blowing agent, extrusion conditions must also be chosen carefully in order to avoid such obstacles as skin formation. There are various types of post-treatment for converting closed cell foams to open cell foams, which essentially entails removing a thin membrane between the cells or pores. One method involves heat treatment. By treating the closed cell foam in a controlled, elevated temperature environment, it is possible to melt the thin membrane without melting the rest of the material. The temperature depends on the graft material. Another method for converting closed cell foams to open cell foams is a mechanical method. By crushing the closed cell foam between rollers or a similar device, the thin membrane will rupture due to the pressure in the pore. A third method is another mechanical method wherein explosive gasses (e.g. stoichiometric ratios of $O_2/H_2$) are infiltrated into the pores. The cells are ruptured by ignition of these gasses. Yet another method is a chemical method whereby the foam is subjected to hydrolysis, thereby destroying the thinner membranes more rapidly than the thicker ribs defining the pores. Any of these methods can be used alone or in combination to produce open cell foams.

Yet another method for producing the graft of the invention is a particle and fiber extraction technique using a layered method. This method is illustrated in FIGS. 2 and 3a–3f. In this method, a paste 30 is prepared from a graft material solution and an extractable filler, wherein the graft material solution comprises a graft material and a graft material solvent. As in the coating solution of the fiber winding and extraction technique, the suitable graft materials include thermoplastic elastomers, particularly thermoplastic polyurethanes, such as Pellethane, Biomer type polyurethanes, Chronoflex, and Hydrothane; and suitable graft material solvents include N-methyl pyrrolidone (NMP) and 1-methyl-2-pyrrolidinone. Suitable materials for the extractable filler include protein beads, e.g. alginate, gelatin, carbohydrates, inorganic and organic salts.

Figure 2:
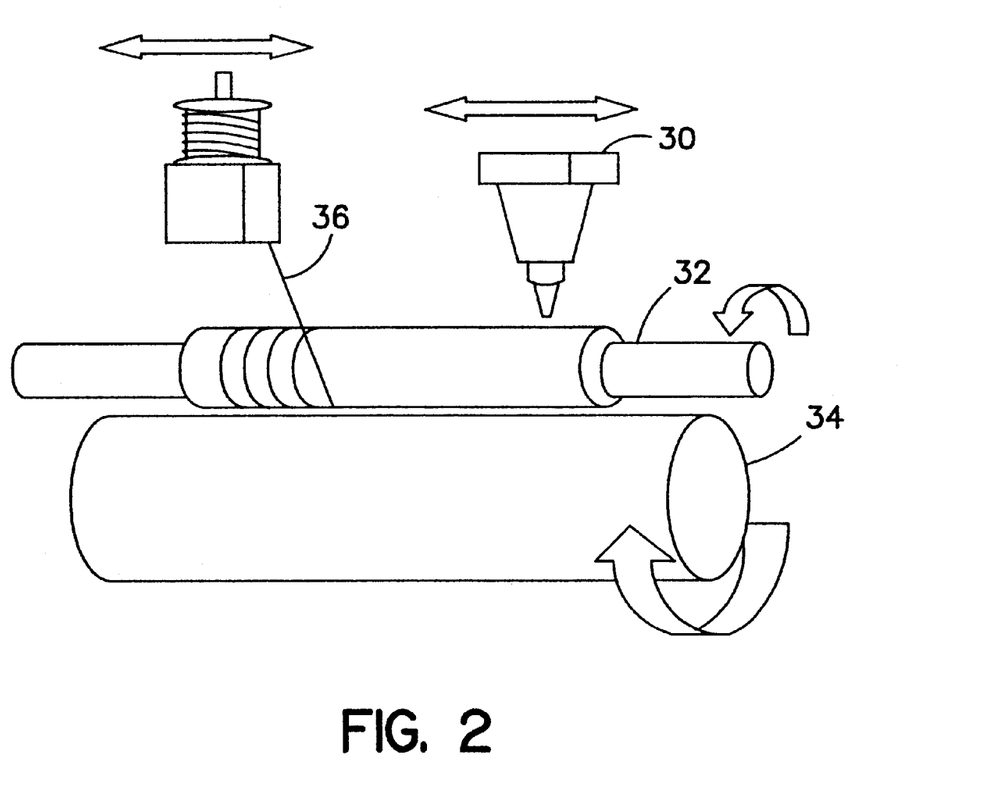
FIG. 2 is a schematic drawing of an alternate method of producing the synthetic vascular graft of the invention.

A layer of the paste 30 is deposited onto a mandrel 32 having a diameter about equal to a desired internal diameter of a resulting graft. The internal diameter of the graft is preferably between 1 mm and 20 mm, more preferably in the range of 2 to 6 mm for small diameter vessel replacement. The paste 30 is pressed onto the mandrel 32 with a roller 34. An extractable fiber 36 is wound onto the paste layer. The extractable fiber 36 is made of alginate, gelatin, carbohydrates, inorganic or organic salts, for example. Additionally, a non-extractable fiber, as described in the fiber winding and extraction technique, can be wound onto the mandrel for reinforcement. Additional layers of the paste 30 alternating with additional layers of the wound extractable fiber 36, with or without a reinforcing fiber, are deposited onto the mandrel 32 until a desired graft thickness is achieved. The thickness of the paste 30 can vary from 0.1 to 5 mm, more preferably from 0.4 to 1.5 mm, depending on the diameter of the graft. The graft can be made with as few as two layers of the paste 30, with one layer of the wound extractable fiber 36 between the two paste layers.

Figure 3A:
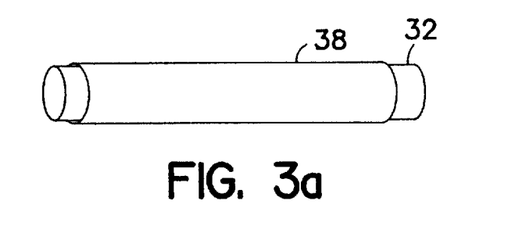
FIGS. 3a–3f are a series of perspective views of a mandrel from FIG. 2 as the method is carried out.
Figure 3B:
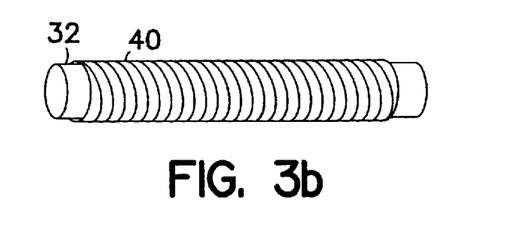
Figure 3C:
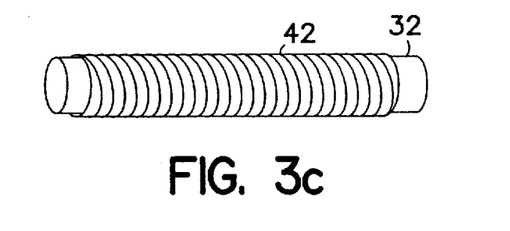
Figure 3D:
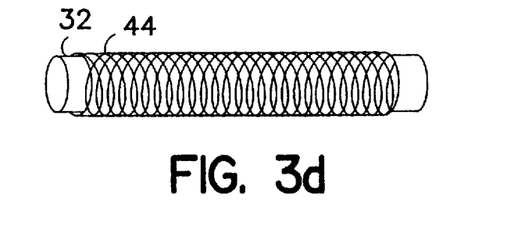
Figure 3E:
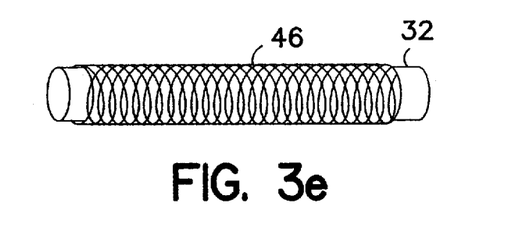
Figure 3F:
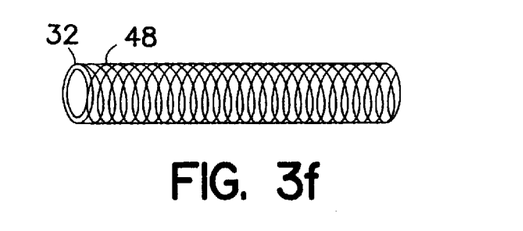

Progressive stages of the mandrel 32 as the method is carried out are shown in FIGS. 3a–3f. FIG. 3a shows a first layer of paste 38 rolled onto the mandrel 32. In FIG. 3b, a first fiber 40 is wound onto the first layer of paste 38. FIG. 3c shows a second layer of paste 42 covering the first layer of paste 38 and the first fiber 40. In FIG. 3d, a second fiber 44 is wound onto the second layer of paste 42. FIG. 3e shows a third layer of paste 46 covering the first two layers of paste 38 and 42 and the first two wound fibers 40 and 44. In FIG. 3f, a third fiber 48 is wound onto the third layer of paste 46.

The graft material solution is then precipitated by phase precipitation, wherein the graft is immersed into a precipitation solvent, and/or by drying. Examples of suitable precipitation solvents include water, ethanol, acetone, or combinations of any of these. The extractable fiber 36 and extractable filler are extracted, either simultaneously or consecutively, by applying a fiber extraction solvent to produce channels in the space occupied by the extractable fiber 36. A filler extraction solvent can be the same solvent as the fiber extraction solvent, and may vary only in temperature, e.g. a cold water filler extraction solvent and a warm water fiber extraction solvent. The precipitation and extraction can be effected either simultaneously or consecutively.

A further method for producing the graft of the invention is a particle and fiber extraction technique using a continuous method. Like the layered method, described above, the continuous method entails preparing a paste 30 from a graft material solution and an extractable filler, and layering the paste 30 and an extractable fiber 36 onto a mandrel 32, as shown in FIG. 2. However, in this method, the paste 30 is deposited onto the mandrel 32 simultaneously while the extractable fiber 36, with or without a reinforcing, non-extractable fiber, is wound onto the mandrel 32. As in the layered method, the graft material solution is then precipitated and the extractable fiber 36 and extractable filler are extracted, either simultaneously or consecutively.

The above-described methods can also be used to produce other items, such as a biosynthetic, whole-root aortic valve prosthesis.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A vascular graft prosthesis comprising:
   an elastomeric polymeric tubular structure having a wall; and helically oriented, interconnected transmural ingrowth tubular channels formed from extractable fiber in the tube wall.

2. The vascular graft prosthesis of claim 1 wherein the tubular structure has an internal diameter in a range of 1–20 mm.

3. The vascular graft prosthesis of claim 1 wherein the tubular structure has an internal diameter in a range of 2–6 mm.

4. The vascular graft prosthesis of claim 1 wherein the diameters of the channels are in a range of 10–300 μm.

5. The vascular graft prosthesis of claim 1 wherein the diameters of the channels are in a range of 40–110 μm.

6. The vascular graft prosthesis of claim 1 wherein the elastomeric polymeric tubular structure comprises polyurethane.

7. The vascular graft prosthesis of claim 1 wherein the elastomeric polymeric tubular structure comprises a segmented aliphatic polyurethane.

8. The vascular graft prosthesis of claim 1 wherein the elastomeric polymeric tubular structure comprises a material selected from the group consisting of Pellethane, Chronoflex, Hydrothane, Estane, Elast-Eon, Texin, Biomer, Surethane, Corethane, Carbothane, Techoflex, Tecothane and Biospan.

9. The vascular prosthesis of claim 1 wherein substantially all of the channels have diameters within 10 μm.

10. The vascular prosthesis of claim 1 wherein the elastomeric polymeric tubular structure comprises PTFE.

11. The vascular graft prosthesis of claim 1 wherein the elastomeric polymeric tubular structure comprises ePTFE.

12. The vascular graft prosthesis of claim 1 wherein the elastomeric polymeric tubular structure comprises Dacron.

13. The vascular graft prosthesis of claim 1 further comprising reinforcing fibers in the elastomeric polymeric tubular structure.

14. The vascular graft prosthesis of claim 13 wherein the reinforcing fibers have diameters in a range of 10 to 100 micrometers.

15. The vascular graft prosthesis of claim 13 wherein the fibers used to form the tube wall have diameters with a standard deviation of less than 20 micrometers.

16. The vascular graft prosthesis of claim 13 wherein the fibers used to form the tube wall have diameters with a standard deviation of less than 10 micrometers.

17. The vascular graft prosthesis of claim 13 wherein the reinforcing fibers comprise an elastic, non-degradable material.

18. The reinforcing fibers of claim 17 further comprising a material degradable in vivo.

19. The vascular graft prosthesis of claim 13 wherein the reinforcing fibers comprise a non-elastic, non-degradable material.

20. The reinforcing fibers of claim 19 further comprising a material degradable in vivo.

21. The reinforcing fibers of claim 19 further comprising an elastic, non-degradable material.

22. The reinforcing fibers of claim 21 further comprising a material degradable in vivo.

23. An aortic valve prosthesis comprising:
   an elastomeric polymeric tubular structure having a wall; and helically oriented, interconnected transmural ingrowth tubular channels formed from extractable fiber in the tube wall.

* * * * *

UNITED STATES PATENT AND TRADEMARK OFFICE
CERTIFICATE OF CORRECTION

PATENT NO.        : 6,540,780 B1                                         Page 1 of 1
APPLICATION NO. : 09/434,071
DATED             : April 1, 2003
INVENTOR(S)       : Peter P. Zilla and Deon Bezuidenhout It is certified that error appears in the above-identified patent and that said Letters Patent is hereby corrected as shown below:

Col. 10, Line 7:   ...."vascular prosthesis"......   should read   ...--vascular graft prosthesis--....
Col. 10, Line 9:   ...."vascular prosthesis".....    should read   ....--vascular graft prosthesis--...

Signed and Sealed this

Twenty-fifth Day of December, 2007

JON W. DUDAS
*Director of the United States Patent and Trademark Office*